United States Patent [19]
Miyano et al.

[11] Patent Number: 4,801,610
[45] Date of Patent: Jan. 31, 1989

[54] PHENOLIC ESTER DERIVATIVES AS ELASTASE INHIBITORS

[75] Inventors: Masateru Miyano, Northbrook; James R. Deason, Wilmette, both of Ill.

[73] Assignee: G. D. Searle & Co., Chicago, Ill.

[21] Appl. No.: 58,467

[22] Filed: Jun. 5, 1987

Related U.S. Application Data

[63] Continuation of Ser. No. 612,193, May 21, 1984, Pat. No. 4,683,241.

[51] Int. Cl.$^4$ .................... A61K 31/22; A61K 31/265
[52] U.S. Cl. .................................... 514/512; 514/546; 514/548
[58] Field of Search ........................ 560/138, 139, 140; 514/510, 512, 546, 548, 549, 551

[56] References Cited

U.S. PATENT DOCUMENTS 3,632,630  1/1972  Chao et al. ........................ 560/140
4,329,360  5/1982  Resnick ............................ 560/140 X
4,338,334  7/1982  Jensen et al. ................... 514/546 X
4,683,241  7/1987  Miyano et al. .................. 560/139 X

OTHER PUBLICATIONS

Grant, ed., Hackh's Chemical Dictionary, 4th ed., 1969, McGraw-Hill, N.Y., p. 15.

Primary Examiner—Michael L. Shippen
Attorney, Agent, or Firm—Mary Jo Kanady; Paul D. Matukaitis

[57] ABSTRACT

Phenolic esters of the general formula I

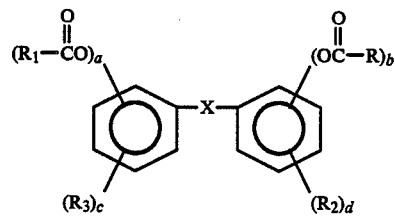

are useful for the prevention, management or alleviation of elastase mediated diseases or conditions.

1 Claim, No Drawings

PHENOLIC ESTER DERIVATIVES AS ELASTASE INHIBITORS

This is a continuation of application Ser. No. 612,193, filed May 21, 1984, now U.S. Pat. No. 4,683,241.

BACKGROUND OF THE INVENTION

Proteases or protein splitting enzymes are proteins whose function is to alter or decompose other proteins by splitting them into fragments. They are essential in a variety of physiological activities such as digestion, formation and dissolution of blood clots, the repair or removal of damaged or injured tissues, the removal of tissue debris, the immune reaction to foreign cells and organisms and inflammatory processes among others.

While the proteases serve important biological functions, they are controlled by a mechanism which prevents them from indiscriminately destroying any protein within their presence. The mechanism includes protease inhibitors which bind with the proteases and prevent their protein fragmentation action. For further information, see "A Family of Protein cutting Proteases", Scientific American, R. M. Stroud, July 1974, pages 74-78.

In general, proper function of the control mechanism is important for the health of the host organism. A protease-inhibitor imbalance can produce an excess of protease and permit the undesirable degradation of structural proteins such as elastin, collagen, and proteoglycan. It can be seen that dysfunction of the control mechanism can lead to connective tissue destruction and disease.

The protease, elastase, is believed to play an important part in the etiology of inflammatory connective tissue disease. It fragments elastin, a functional protein component of connective tissue, as well as other proteins and, hence, can reduce the elastic expansion and contraction of the lungs and the cardiovascular system and can destroy the resiliency and elasticity of joints. As a result, the function, elasticity and resiliency of organs containing elastin can be adversely affected and the organs will eventually undergo trophic changes, including the loss of elastic tissue, as occurs in such diseases as rheumatoid arthritis, pulmonary emphysema, chronic obstructive pulmonary disease, atherosclerosis, pseudoxanthoma elasticum, X-linked cutis laxa, Menke's kinky-hair syndrome, and Ehlers-Danlos syndrome, Type V.

Further indications of the relation between elastase and connective tissue disease have been shown by animal model studies and by joint tissue studies. For example, papain and porcine pancreatic elastase are elastase-like proteases which have been used experimentally to produce emphysema-like disease in animal models. Human leukocyte elastase, extracted from human polymorphonuclear leukocytes, has also been instilled intratracheally into animals to produce a disease resembling human emphysema. The physiological and morphological results of elastase induced emphysema in such animal models and the corresponding animal symptoms and biochemistry have been compared to the disease in man, and these tests have shown an association between elastase and emphysema; see Sandberg, et al., The New England Journal of Medicine, 304, 566, (1981).

Rheumatoid arthritis is another example of a disease which has been linked to inhibitor-protease imbalance. In the course of this disease, polymorphonuclear leukocytes are released and enter acute inflammatory exudates to phagocytize immune reactants and cellular material thereby releasing elastase. When the elastase release overwhelms the inhibitors present in the local tissue, phagocytosis proceeds not only upon material which should be removed but upon the healthy tissue and hence causes greatly enhanced tissue damage. The major portion of this proteolytic activity has been attributed to elastase. See, for example, Janoff, Biochem. J., 114, 157 (1969) and Wong, Travis, Biochem. Biophys. Res. Comm., 96, 1449 (1980).

Research into inflammatory diseases involving proteolytic enzymes has sought to isolate and characterize endogenous protease inhibitors present in biological tissues. Human serum $\alpha_1$-antitrypsin and $\alpha_2$-macroglobin are two known endogenous inhibitors. Synthetic inhibitors have also been studied; see U.S. Pat. No. 4,195,023. In general, however, little work has been done to produce a synthetic inhibitor which is highly active, produces desirable results in models of elastase related disease and is relatively free of harmful side effects.

SUMMARY OF INVENTION

It is, therefore, an object of the invention to produce a synthetic inhibitor of proteolytic enzymes which will be effective for the alleviation or prevention of diseases associated with protease-inhibitor control imbalance. A further object is the production of a synthetic inhibitor compound which inhibits elastase action. Yet another object of the invention is the production of a synthetic inhibitor of elastase which has specific activity and exhibits few side effects.

These and other objects are achieved according to the compounds, compositions and methods of the invention comprised of the phenolic ester derivatives of formula I having elastase inhibitor activity:

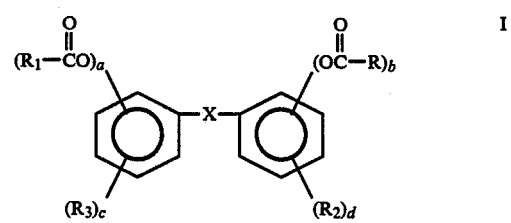

wherein
R and $R_1$ are the same or different and represented by $C_2$-$C_6$ alkyl, $C_1$-$C_6$ alkoxy, $C_3$-$C_6$ cycloalkyl, $C_2$-$C_6$ acylaminoalkyl, $C_2$-$C_6$ alkenyl, $C_2$-$C_6$ carboxyalkyl or $C_3$-$C_{10}$ alkoxycarbonylalkyl;

$R_2$ and $R_3$ are the same or different and represent hydroxy, halogen, $C_2$-$C_4$ alkyl, $C_1$-$C_4$ alkenyl, $C_1$-$C_4$ hydroxyalkyl, $C_2$-$C_6$ carboxyalkyl, pyranyloxy, or $C_2$-$C_4$ formylalkyl;

X represents a group selected from

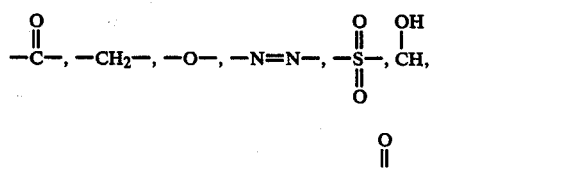

together with the benzene rings represents the group

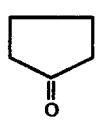

a, b, c and d are integers ranging between about 0 to 4 provided that at least one of a-b is 1 and the pharmaceutically acceptable non-toxic salts or adducts thereof.

DETAILED DESCRIPTION OF THE INVENTION

Proteolytic enzymes are of great importance for all mammalian organisms. The many physiological and biochemical processes in which they function require substantial control of their proteolytic activity. While the proteolytic enzymes hydrolyze peptide bonds of proteins, the nature of the active catalysis site of each type of proteolytic enzyme varies so that the electrostatic, hydrophilic and lipophilic forces which bind an enzyme to its substrate can be utilized to permit specific rather than general protein hydrolysis. Further control is produced by protease inhibitors which have evolved configurations within the binding regions which closely resemble those of bound substrate proteins. Since proteolytic enzymes are ubiquitous and serve such an important function for biological organisms, a non-specific synthetic inhibitor which prohibits the action of many proteolytic enzymes would serve little purpose as a drug. Instead, inhibition or control of a specific proteolytic enzyme is the desired goal.

It has now been found, in accordance with the present invention, that the compounds of formula I advantageously selectively inhibit the proteolytic enzyme elastase from human leukocytes. Without wishing to be limited to any particular mechanism of action, it is presently believed that the probable mechanism of action of the compounds of the present invention is through species specific substrate elastase binding as depicted below:

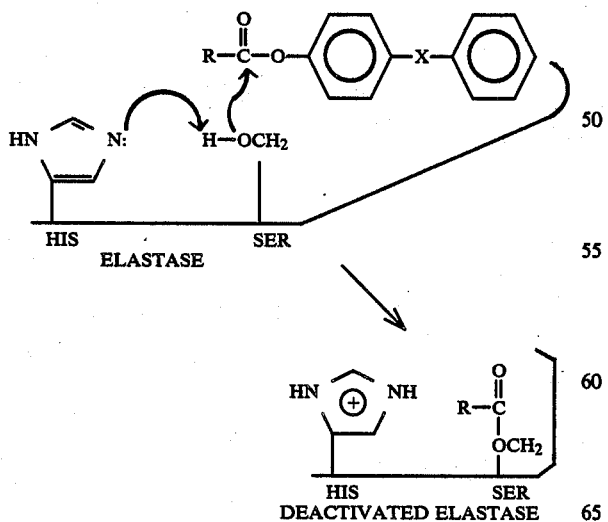

Consistent with the foregoing postulated mechanism of action and the apparent steric configurations attendant elastase inhibitory ativity, the compounds of the present invention are comprised of those having the formula I

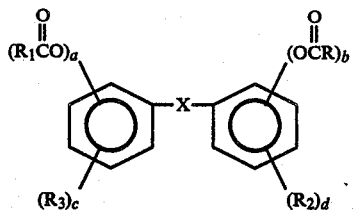

wherein
R and $R_1$ are the same or different and represented by $C_2$-$C_6$ alkyl, $C_1$-$C_6$ alkoxy, $C_3$-$C_6$ cycloalkyl; $C_2$-$C_6$ acylamino, $C_2$-$C_6$ alkenyl, $C_2$-$C_6$ carboxyalkyl or $C_3$-$C_{10}$ alkoxycarbonylalkyl; $R_2$ and $R_3$ are the same or different and represent hydroxy, halogen, $C_1$-$C_4$ alkyl, $C_1$-$C_4$ alkenyl, $C_1$-$C_4$ hydroxyalkyl, $C_2$-$C_6$ carboxyalkyl, pyranyloxy, or $C_2$-$C_4$ formylalkyl;
X represents a group selected from

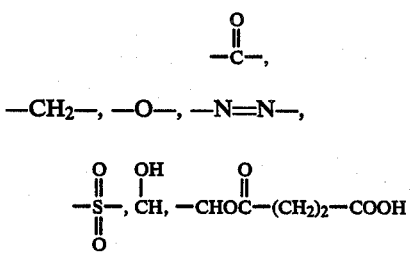

or together with the benzene rings represents the group

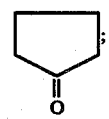

a, b, c and d are integers ranging between about 0 to 4 provided that at least one of a-b is 1 and the pharmaceutically acceptable non-toxic salts thereof.

Of the foregoing compounds, particularly preferred for use in the elastase inhibitory/anti-inflammatory pharmaceutical compositions and methods of the invention are those compounds of formula II and the pharmaceutically acceptable nontoxic acid ester salts thereof:

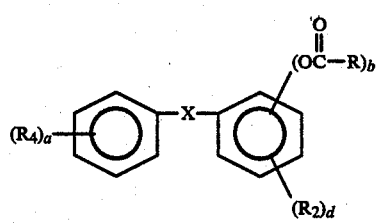

wherein
R represents $C_3$-$C_6$ alkyl, $C_2$-$C_4$ alkenyl, $C_1$-$C_4$ alkoxy, $C_2$-$C_4$ alkenyl, $C_2$-$C_4$ carboxyalkyl or $C_3$-$C_6$ alkoxycarbonylalkyl;

$R_2$ represents $C_2$-$C_4$ alkenyl, $C_1$-$C_4$ hydroxyalkyl or $C_2$-$C_4$ formylalkyl $R_4$=R or halogen or hydroxy;

X represents

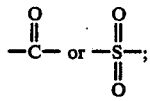

and a-b and d are as defined before.

Exemplary of particularly preferred substituents within the foregoing structural definitions for formula II are as follows:

R=—CH(CH$_3$)$_2$, —C(CH$_3$)$_3$, —CH$_2$CH(CH$_3$)$_2$,

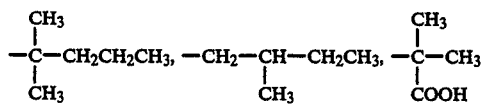

$R_2$=—CH$_2$—CH=CH$_2$, —(CH$_2$)$_3$OH, —(CH$_2$)$_2$COOH,

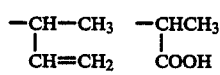

$R^4$=—C(CH$_3$)$_3$, OH

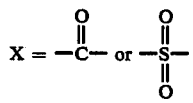

a=0 or 1
b=1, 2 or 3
d=0 or 1

As used herein, the expression "alkyl" in reference to the defined groups includes straight or branched chain carbon-carbon linkages with the proviso that when R is alkyl R is other than methyl. Preferred alkyl moieties include isopropyl, isobutyl, secondary butyl and tertiary butyl.

It will also be appreciated by those skilled in the art that the phenolic ester derivatives of formulas I and II as defined hereinabove are capable of forming bis-adducts, depending upon reaction conditions, and these adducts likewise comprise active elastase inhibitors within the scope of the present invention. Exemplary of such adducts are those of formulas III and IV:

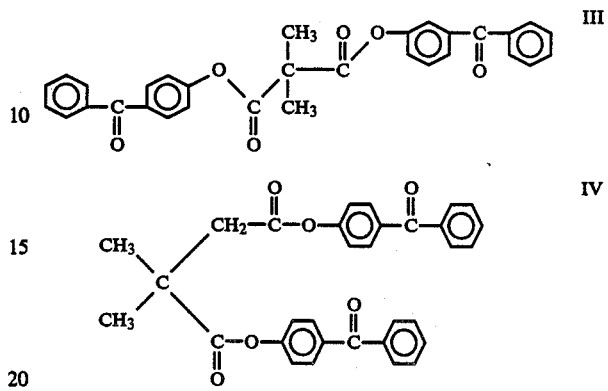

The compounds of the invention can be facilely prepared by synthetic methods known in the art from available starting materials. For example, the acyloxy moieties corresponding to

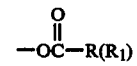

may be prepared by conventional esterification procedures from the preselected phenolic starting materials having the hydroxyl group corresponding to the desired ring position for the ultimate ester, (i.e., 2-hydroxy,4 or 4'-hydroxy, etc.) reacted with the desired ester precursor, e.g., trimethylacetyl chloride (pivaloyl ester), isobutyryl chloride (isobutyryl ester), methacryloyl chloride (methacryloyl ester), etc. In like manner those derivatives bearing the $R_2$, $R_3$ and $R_4$ etc. substituents or a plurality of same will be prepared.

The following general reaction schemes (A-F) depict the synthetic methods which will be utilized in the preparation of the compounds of the present invention with appropriate selection of specific reactants and reaction conditions to obtain the particular compounds of formula I as more specifically detailed in the examples indicated.

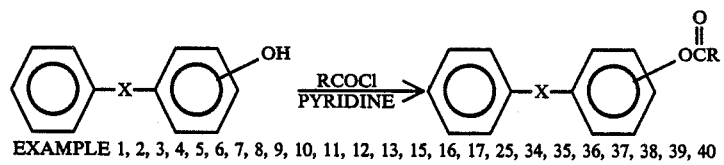

EXAMPLE 1, 2, 3, 4, 5, 6, 7, 8, 9, 10, 11, 12, 13, 15, 16, 17, 25, 34, 35, 36, 37, 38, 39, 40

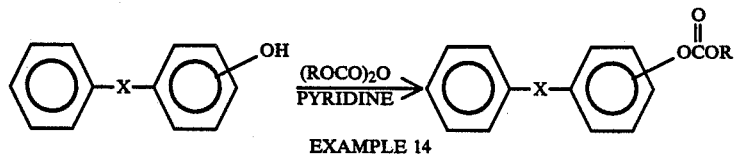

EXAMPLE 14

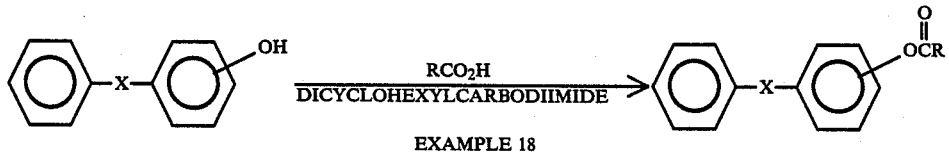

EXAMPLE 18

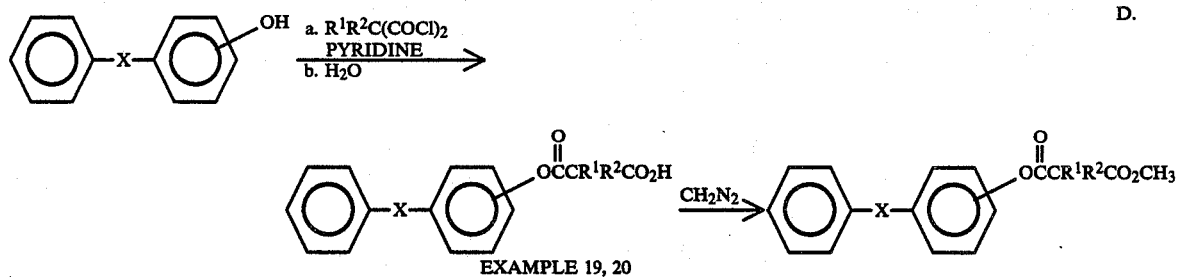

D.

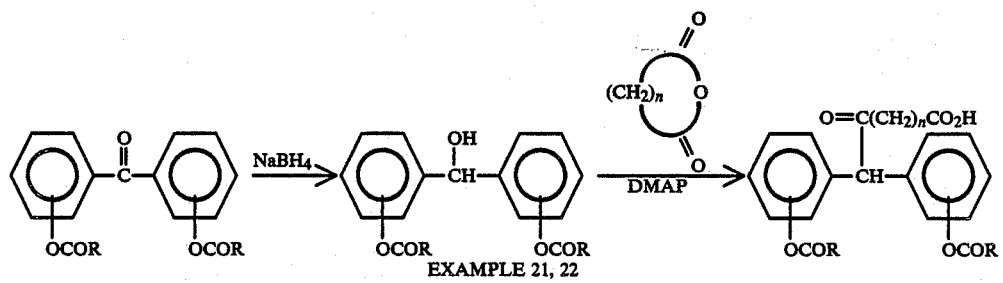

E.

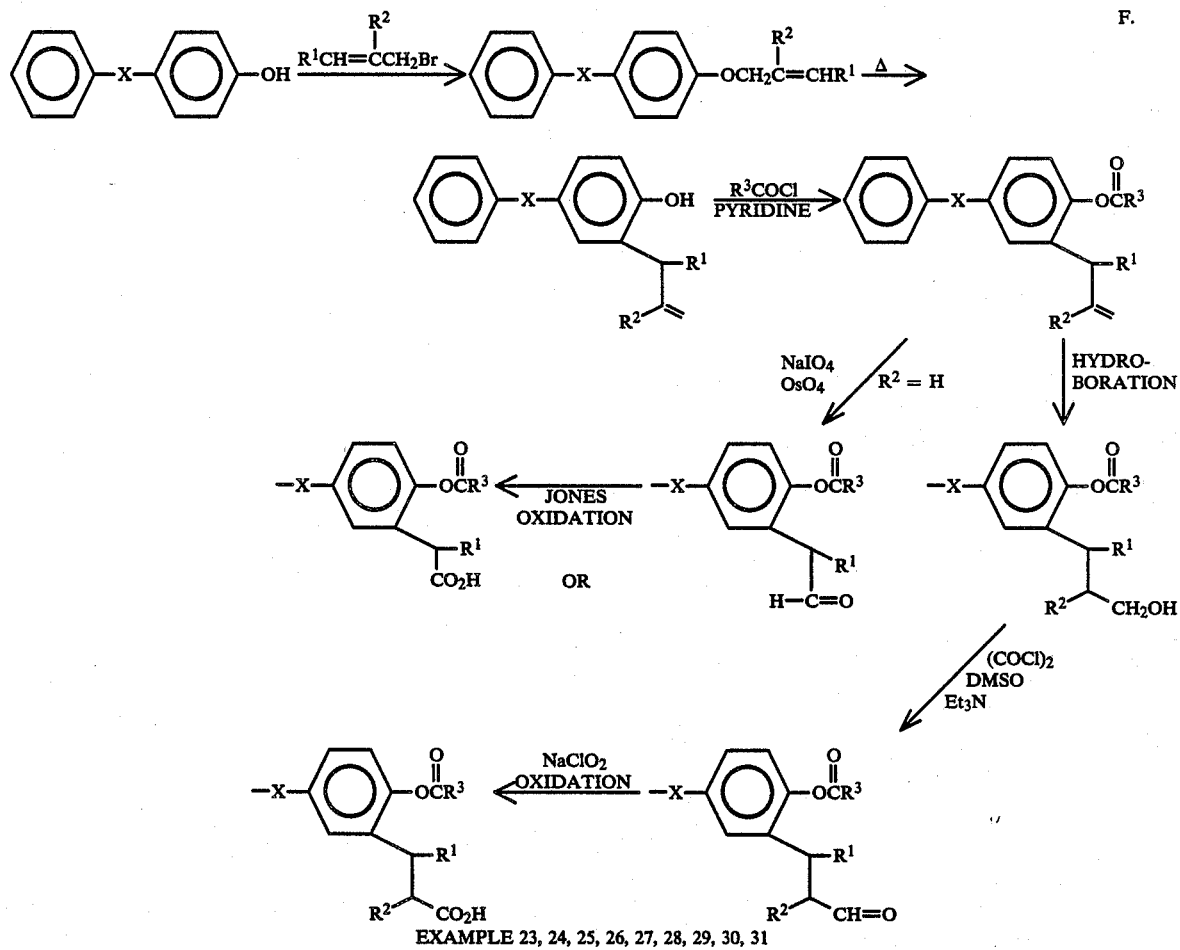

Further, it will be appreciated by those skilled in the art that the compounds of the present invention may be prepared in various salt forms and, as used herein, the expression "pharmaceutically acceptable non-toxic salts" is intended to include all those salts capable of being formed with the present compounds and substituted derivatives thereof in accordance with the invention without materially altering the chemical structure or pharmacological activity of the parent compounds. For example, alkali metal salts of carboxylic acid derivatives of the invention may be obtained by reaction with suitable bases, e.g., sodium hydroxide, potassium hydroxide, etc. Likewise alkaline earth metal salts, acid addition salts and the like may be obtained, where necessary to, for instance, alter solubility properties, etc.

During the progression of connective tissue diseases such as emphysema, arthritis, atherosclerosis and others, vast numbers of human protease secreting cells, for example, immune system cells such as neutrophils, are believed to be attracted to the diseased tissue where they engage in phagocytosis of locally generated complexes and tissue debris. During this process proteolytic enzymes are released into the intercellular spaces to promote phagocytosis. These enzymes, such as elastase, have the capacity to degrade connective tissue, bronchial collagenous membranes, synovial cartilage, and arterial elastic lamellae. Although this action is normal, protease imbalance and a subsequent overproduction of active protease is believed to contribute in a major way to irreversible destruction of the tissue especially in chronic inflammatory conditions. Consequently, controlling the protease imbalance with an inhibitor which mimics natural, physiological control is helpful for the prevention or alleviation of protease related diseases.

The derivatives of the invention are such protease inhibitors and act as pharmacologically active agents for the prevention or alleviation of protease related diseases. These derivatives can prevent tissue injury by their action as controlling inhibitors of active proteolytic enzymes. In particular, the derivatives are useful to prevent or alleviate malconditions related to or arising from human leukocyte elastase imbalance and harmful degradation of elastin and other proteins. Such diseases would include emphysema, atherosclerosis, connective tissue disease, rheumatoid arthritis, rheumatoid joint disease, pseudoxanthoma elasticum, X-linked cutis laxa, Menke's kinky-hair syndrome and Ehlers-Danlos syndrome, Type V as well as other diseases resulting from the harmful effect of elastase.

Several biochemical and animal model tests can be used to examine the ability of the derivatives of the invention to prevent or alleviate the harmful biological action of elastase. The biochemical assays permit direct measurement of drug controlled inhibition of elastase fragmentation of proteins. Typical tests include a chymotrypsin/t-Boc-Tyr-p-Nitrophenyl ester incubation, a human leukocyte elastase-Methoxysuccinyl-Ala-Ala-Pro-Val-Nitroanilide incubation and a hog pancreatic elastase/ t-Boc-L-Ala-p-Nitrophenol ester incubation. In these tests, protease reaction with the substrate is measured in the presence and absence of the drug to be tested. Inhibition of protease action is indicated by a decrease in the amount of substrated fragmented. The basic parameters for such biochemical assays have been reported in the literature: J. Biol. Chem., 255, 5435 (1980); Biochem. Biophys Acta., 268, 257 (1973); Anal. Biochem. 48,9 (1972); and Biochemistry, 20, 3675 (1981).

In general, in vivo animal model tests will also permit estimation of drug controlled inhibition of protease action and in addition allow assessment of the decrease in tissue damage caused as a result of drug-protease interaction. Some animal tests commonly used include emphysema models such as mouse lung challenge with aspirated elastase solution and mouse or hamster intrabronchial challenge with papain, porcine pancreatic elastase or neutrophil elastase. In these procedures, the test drug is administered shortly before or after protease challenge, the animal is examined for respiratory compliance and sacrificed about 6–10 days later, and the lungs examined for lesions. Since it is believed that the compounds of formula I promote specific inhibition of neutrophil elastase, animal model tests would employ this elastase in order to develop an estimate of derivative activity. Such methods have been described in Am. Rev. Resp. Dis., 121, 1025 (1980); Lab. Invest., 34, 372 (1976); New Eng. J. Med., 304, 566 (1981); U.S. Pat. No. 4,195,025.

Examination of the derivatives of the invention in a selection of these tests has shown that they are therapeutically active compounds useful for the treatment of elastase mediated disease conditions. In particular, the derivatives of the invention are active inhibitors of human leukocyte elastase in the biochemical human leukocyte elastase-substrate assay while showing much lower ihhibition in the chymotrypsin and hog pancreatic elastase biochemical assays. The derivatives also show few side effects as they do not produce significant activity in such tests as metrazol antagonism of mouse central motor coordination, mouse diuresis and hCG stimulation of luteal cell progesterone production as well as other similar biological test screens.

The derivatives of the invention can be used in the treatment of emphysema, arthritis, atherosclerosis and other connective tissue diseases. Although the treatment of an individual patient suffering such a malady will be based upon his unique condition and upon the judgment of his attending physician, in general, the derivatives can be administered in doses and by routes which would be effective for the alleviation or prevention of such diseases. For treatment of arthritis, atherosclerosis and other internal connective tissue organ diseases, therapeutically effective amounts of the derivatives which would substantially inhibit elastase action may be injected intravenously, subcutaneously, intramuscularly or intraperitoneally or may be administered orally or rectally. For treatment of acute, localized arthritis, therapeutically effective amounts of the derivatives which would substantially inhiit elastase action may be injected directly into the inflamed tissue, e.g., intra-articular, or may be administered by any of the aforementioned routes. For treatment of emphysema, therapeutically effective amounts of the derivatives which would substantially inhibit elastase action may be administered as a bronchial aspiration or mist directly to the lung or may be administered orally or rectally or injected intravenously, intramuscularly, subcutaneously or intraperitoneally. For treatment of chronic dermal connective tissue malconditions, therapeutically effective amounts of the derivatives which would substantially inhibit elastase action may be applied topically or systemically administered by oral, rectal or infection routes.

With these general guidelines in mind, the compounds for use in the elastase inhibitory pharmaceutical compositions and methods of the present invention are administered to an animal in need thereof in an amount sufficient to promote therapeutically effective elastase inhibition. The following dosage ranges may be employed as therapeutically effective elastase inhibitors in the treatment, management or alleviation of such elastase mediated conditions, diseases or disorders. Oral or rectal administration may be accomplished with a dose of derivatives of about 100 to 1000 mg per dosage unit with about 2 to 6 doses per day being given. Injection may be accomplished with a dose of about 50 to 500 mg per dosage unit with about 3 to 4 doses per day being given. Bronchial administration may be accomplished with aerosols or mists containing from about 0.1 to 10 percent derivative with a dose of about 5 to 200 mg per dosage unit being given from 2 to 6 times per day. Topical or transdermal administration may be accomplished with a dose of about 5 to 500 mg per dosage unit with about 1 to 3 applications per day. Variation and adjustment in dosing and administration will follow parameters known for each route of administration.

According to the invention the derivatives may be used either alone or in combination with a suitable pharmaceutical carrier. Used alone they may be administered as an alcoholic or aqueous solution, suspension or dilution at the appropriate dosage level and concentration. The character of such solutions will be adjusted for the route of administration desired.

The derivatives may be combined with such pharmaceutical carriers as: elixirs, suspending agents, diluents, starches, sugars, absorbing agents, wetting agents, isotonic agents, drying agents, waxing agents, solubilizing agents, dissolving aids, disintegrating aids, transport agents, and other similar pharmaceutical agents known to those skilled in the art. Examples include lactose, sucrose, carregeenin, gelatin, potato starch, corn starch, tapioca starch, gum arabic, magnesium stearate, stearic acid, agar, pectin, acacia, ethanolic solutions, citric-carbonate buffers, isotonic solutions, peanut oil, olive oil, sesame oil, methyl cellulose, polyvinylpyrrolidine, cocoa butter, polyethylene glycol, and other similar types of well known pharmaceutical carriers, adjuvants, excipients, etc. (collectively referred to herein as "carriers").

Solutions, suspensions or dilutions of the compounds of the invention and pharmaceutical compositions of the invention may be formulated using appropriate known pharmaceutical methods to produce dosage forms appropriate for the desired route of administration. Such forms include capsules, tablets, sterile or isotonic solutions, injectable solutions, aerosol emulsions, liquid suspensions, troches, suppositories, oral liquids, syrups, sugar coated tablets, enteric coated tablets, combination tablets, sustained-release capsules and tablets, sustained-release micro-encapsulation using pharmacologically acceptable sustained release polymers, and other similar formulations and or otherwise dosed medicaments known to those skilled in the art. When used intrabronchially, the formulation may be sprayed with an inhaler, atomizer, nebulizer and the like.

The following non-limiting examples will further illustrate to those skilled in the art the details for the preparation and biological testing of the derivatives of the invention. All temperatures are in °Celsius unless otherwise stated.

EXAMPLE 1

4-pivaloyloxybenzophenone

A solution of 2.0 g (1 mmol) of 4-hydroxybenzophenone and 1.25 g (1.5 mmol) of trimethylacetyl chloride in 30 ml of pyridine was heated to 50° C. for 2 h. The reaction mixture was stripped of most of the pyridine and then slurried into water. The crude product obtained by filtration was air-dried and recrystallized from ethanol. The first crop (2.35 g, 79.9%, M.P.≈100°-102° C.) was used for analysis and biological evaluation.

Anal. Calcd. for $C_{18}H_{18}O_3$: C, 76.57; H, 6.43. Found: C, 76.54; H, 6.23.

EXAMPLE 1a 4,4'-dipivaloyloxybenzophenone

A solution of 10 g of 4,4' dihydroxybenzophenone in pyridine (40ml) was treated with trimethylacetyl chloride and refluxed for 5 hours. The resultant solution was concentrated under reduced pressure and ETOAc added. The organic layer was washed with $H_2O$, 5% aq. $K_2CO_3$, 1% aq. NaOH and dried over $MgSO_4$ and concentrated to give approximately 13 g of a beige solid which was further chromatographed using 7/93 ethyl acetate-toluene to yield 2.83 g (20%) of the monoester (a) and 3.42 g (19%) (b) of the title compound; M.P.=166°-167° C.

Anal. Calcd. for $C_{18}H_{18}O_4$(a): C, 72.47; H, 6.08. Found: C, 72.05; H, 6.04 Anal. Calcd. for $C_{23}H_{26}O_5$(b): C, 72.23; H, 6.85. Found: C, 72.22; H, 6.81

EXAMPLE 2

2,4,4'-tripivaloyloxybenzophenone

A solution of 2.3 g (0.01 mole) of 2,4,4'trihydroxybenzophenone was warmed to 50° C. with 3.65 g (0.035 mole) of pivaloyl chloride in 75 mls of dry pyridine. After 2 hrs. at 5° C., the solvent was evaporated under $N_2$ stream and $H_2O$ added to the residue. The oily material was extracted with $CH_2Cl_2$ and washed with dilute $K_2CO_3$. The organic layer was dried over $MgSO_4$. The glass which was recovered after solvent removal was crystallized from ethanol; 4.20 g (86%) yield; M.P.~94°-96° C.

Anal. Calcd. for $C_{28}H_{34}O_7$: C, 69.69; H, 7.10. Found: C, 69.99; H, 7.11.

EXAMPLE 3

2,2',4,4'-tetrapivaloyloxybenzophenone

A solution of 2.4 g (0.01 mole) of 2,2',4,4'-tetrahydroxybenzophenone and 5 g (0.04 mole) of pivaloylchloride was warmed to 50° C. in 75 mls of dry pyridine for 2 hrs with a drying tube attached. The solvent was removed via rotary evaporator and the residue was partitioned between $H_2O$ and $CH_2Cl_2$; the organic layer was washed with dilute $K_2CO_3$ and dried over $MgSO_4$. After removal of solvent via rotary evaporation, the title compound was crystallized from ethanol. 4 g. (69%) yield. M.P.~154°156° C.

Anal. Calcd. for $C_{33}H_{40}O_9$: C, 68.26; H, 6.94. Found: C, 67.82; H, 7.16.

EXAMPLE 4

4,4'-dipivaloyloxyazobenzene 1 g (0.0047 mole) of 4,4'-dihydroxyazobenzene and 2 g (0.016 mole) of pivaloyl chloride was stirred in 20 mls of pyridine for 24 hrs. at room temperature. The solvent was blown off under a stream of $N_2$. Water was added and the crude product filtered and recrystallized from ethanol; 1.5 g (83%) yield. M.P.~185°-188° C.

Anal. Calcd. for $C_{22}H_{26}N_2O_4$: C, 69.09; H, 6.85, 7.33. Found: C, 68.68; H, 6.77; N, 7.33.

EXAMPLE 5

2,7-dipivaloyloxyfluorenone 2.1 g (0.01 mole) of 2,7-dihydroxyfluorenone and 2.5 g (0.025 mole) of pivaloyl chloride were warmed to 50° C. in 6 mls of pyridine in a drying tube attached for 2 hrs. The solvent was removed via rotary evaporator and $H_2O$ was added. The crystals were filtered and air dried. Recrystallized from ethanol; 3 g (79%); M.P.~174°-175° C.

Anal. Calcd. for $C_{23}H_{24}O_5$: C, 72.61; H, 6.36. Found: C, 72.20; H, 6.27.

EXAMPLE 6

4-pivaloyloxy-4'-chlorobenzophenone 2.16 g (0.01 mole) of 4-hydroxy-4'-chlorobenzophenone and 1.2 g (0.015 mole) of pivaloyl chloride in solution were warmed to 50° C. for 3 hrs in 60 mls of dry pyridine with a drying tube attached. The solvent was removed via rotary evaporator and $H_2O$ added. The product was filtered and recrystallized from ethanol; 2.3 g (73%) yield; M.P.~113°-114° C.

Anal. Calcd. for $C_{18}H_{17}O_3Cl$: C, 68.25; H, 5.41; Cl, 11.19. Found: C, 68.06; H, 5.52; Cl, 11.07.

EXAMPLE 7

4,4'-α,α-dimethylvaleroyloxybenzophenone 1 g (0.005 mole) of 4,4'-dihydroxybenzophenone and 2 g (0.015 mole) of α,α-dimethylvaleroylchloride in solution were warmed for 5 hrs. at 50° C. in 50 mls of dry pyridine with a drying tube attached. The solvent was removed via rotary evaporators. Residue was treated with $H_2O$. The gummy crystals were extracted with $CH_2Cl_2$ and washed with $K_2CO_3$. The organic layer was dried over $MgSO_4$. Solvent removal after filtration gave crude product. Recrystallized from ethanol; 1.8 g (82%) yield; M.P.~59°-60° C.

Anal. Calcd. for $C_{27}H_{34}O_5$: C, 73.95; H, 7.81. Found: C, 74.22; H, 7.87.

EXAMPLE 8

2,2',4,4'-tetra(3-methylvaleroyloxy)benzophenone

A solution of 1.2 g (0.005 mole) of 2,4,2',4'-tetrahydroxybenzophenone and 3 g (0.025 mole) of 3-methyl valeroylchloride was warmed to 50° C. for 4 hrs. in 50 mls of dry pyridine. Solvent removal via rotary evaporator left an oil. This was partitioned between $H_2O$ and $CH_2Cl_2$. The organic layer was washed with $K_2CO_3$ solution (5%) and dried over $MgSO_4$. After filtration and solvent removal the product remained an oil; 2.5 g (78%) yield.

Anal. Calcd. for $C_{37}H_{50}O_9$: C, 69.57; H, 7.89. Found: C, 69.47; H, 8.03.

EXAMPLE 9

3,4,5,4',5',6',-hexapivaloyloxybenzophenone 100 mg of 3,4,5,4',5',6'-hexahydroxy benzophenone (0.00036 mole) and 450 MG (0.004 mole) of pivaloyl chloride were warmed to 50° C. in 20 mls of pyridine for 4 hrs. Solvent removed via $N_2$ stream. Water added and extraction of product was done via $CH_2Cl_2$. The organic layer was washed with $K_2CO_3$ (5%) and dried over $MgSO_4$. Solvent removal left an oil. 250 mg. (88%) yield.

Analysis Calcd. for $C_{43}H_{58}O_{13}$: C, 65.97; H, 7.47. Found: C, 65.94; H, 7.89.

EXAMPLE 10

2,4,3',4'5'-pentapivaloyloxy-6-hydroxy benzophenone 300 mg (0.001 mole) of 2,4,6,3',4',5'-hexhydroxybenzophenone was treated with 650 mg (0.0065 mole) of pivaloyl chloride at 50° C. for 3 hrs. in 25 mls of dry pyridine. The solvent was blown off under a $N_2$ stream. Residue was extracted with $CH_2Cl_2$ and washed with $H_2O$. Solvent was dried over $MgSO_4$ and evaporated. Residue placed on 10 g florisil column and eluted with toluene. Product collected 425 mg of a glass. (61% yield.)

Analysis Calcd. for $C_{38}H_{50}O_{12}$: C, 65.31; H, 7.21. Found: C, 65.13; H, 7.29.

EXAMPLE 11

2-pivaloyloxybenzophenone 1 g. (0.005 mole) of O-hydroxybenzophenone was warmed in 25 mls of dry pyridine containing 1 g (0.01 mole) of pivaloyl chloride for 3 hrs. at 50° C. Poured into $H_2O$ containing 2 g of $Na_2CO_3$ and extracted with $EtOAc+Et_2O$ and washed with $H_2O$. After drying over $Na_2SO_4$ and filtration, the product was isolated by evaporation of the solvent. Oily material. 1.2 g. (85%) yield.

Analysis Calcd. for $C_{18}H_{18}O_3$: C, 76.57; H, 6.43. Found: C, 76.68; H, 6.43.

EXAMPLE 12

2,2'-dipivaloyloxybenzophenone 2 g (0.01 mole) of 2,2'-dihydroxybenzophenone was dissolved in 30 mls of dry pyridine and 3 g (0.03 mole) of pivaloyl chloride added and contents warmed for 3 hrs. at 50° C. Solvent was removed by rotary evaporator and $H_2O$ added and crystals filtered. Recrystallized from ethanol, 3.2 g (83%) yield, M.P.~106°-108° C.

Analysis Calcd. for $C_{23}H_{26}O_5$: C, 72.23; H, 6.85. Found: C, 72.09; H, 6.87.

EXAMPLE 13

2,4-dipivaloyloxybenzophenone 2,4-dihydroxybenzophenone 1 g (0.005 mole) was warmed to 50° C. with 1.25 g (0.015 mole) of pivaloyl chloride and 30 mls of dry pyridine solvent removed by rotary evaporation $H_2O+EtOAc+Et_2O$ added and stirred. Layers were separated and the organic layer was washed with 5% $K_2CO_3$, then $H_2O$, then dried over $Na_2SO_4$. Solvent was removed after filtration via rotary evaporator. The resulting oily residue was placed on top of a 15 g florisil column and eluted with toluene. Product isolated by removal of solvent. Oil.

Analysis Calc. for $C_{23}H_{26}O_5$: C, 72.23; H, 6.85. Found: C, 72.21; H, 6.90.

EXAMPLE 14

4,4'-di(t-butyloxycarbonyloxy)benzophenone 2.14 (0.01 mole) of 4,4'-dihydroxybenzophenone and 4.4 g (0.02 mole) of di-tert-butyl dicarbonate in 30 ml of dry pyridine was warmed to 50° C. until evolution of $CO_2$ ceased. (2.0 h) Upon the addition of water, crystals of the title compound were obtained which were crystallized from ethanol; 3.6 g, (86%) yield; M.P.~141°-143° C.

Analysis Calcd. for $C_{23}H_{26}O_7$: C, 66.65; H, 6.32. Found: C, 66.54; H, 6.40.

EXAMPLE 15

2-pivaloyloxy-4'-tetrahydropyranyloxy-benzophenone 3 g (0.01 mole) of 2-hydroxy-4-tetrahydropyronyloxy benzophenone was warmed with 0.21 g (0.01 mole) of pivaloyl chloride and 75 mls pyridine at 40° C. for 2 hrs. Solvent was removed via rotary evaporator. $Et_2O$ and aqueous $NaHCO_3$ was added and the organic layer was separated and dried over $Na_2SO_4$. Chromatography on 100 g of Woelm silica gel using toluene afforded the product as an oil. 2.5 g (65%) yield.

Analysis Calcd. for $C_{23}H_{26}O_5$: C, 72.23; H, 6.85. Found: C, 72.29; H, 6.76.

EXAMPLE 16

4,4'-dipivaloyloxydiphenylether 1 g (0.0056 mole) of 4,4'-dihydroxydiphenyl ether and 1.4 g (0.015 mole) of pivaloyl chloride in 40 mls of pyridine were warmed to 50° C. and $H_2O$ added. The crystals were filtered and air dried and recrystallized from ethanol; 1.35 g (73%); M.P.~126°-127° C.

Analysis Calcd. for $C_{22}H_{26}O_5$: C, 72.33; H, 7.07. Found: C, 71.22; H, 7.04.

EXAMPLE 17

4,4'-dipivaloyloxy-diphenylsulfone and 4-pivaloyloxy-4'-hydroxydiphenylsulfone.

A solution of 15.0 g of 4,4'-sulfonyldiphenol in 60 ml of pyridine was treated with 60 ml of pivaloyl chloride initially at 0°~25° C. and then under relux for 4.5 h. The reaction mixture was stripped of pyridine under reduced pressure and then taken up with methylene chloride. The organic layer was washed with cold 2% hydrochloric acid, with water, and finally with 2% bicarbonate solution. The dried ($MgSO_4$) extract was concentrated (18.9 g) and chromatographed on a silica gel column using methylene chloride ethanol to give the less polar bis-ester (a) (8.5 g; M.P.~190°-192° C.) and the more polar half-ester (b) (4.5 g; M.P.~139°-142.5° C.)

a. Calcd. for $C_{22}H_{26}O_6S$: C,63.14; H, 6.26; S, 7.66. Found: C,63.14; H, 6.32; S, 7.81.

b. Calcd. for $C_{17}H_{18}O_5S$: C, 61.06; H, 5.43; S, 9.59. Found: C, 60.85; H, 5.28; S, 9.53.

EXAMPLE 18

4-(α-methyl-α-acetamino)-propionyloxybenzophenone.

A solution of 2.06 g (10 mmol) of dicyclohexylcarbodiimide in 30 ml of methylene chloride was added to a slurry of N-acetyl-α,α-dimethylglycine (1.45 g, 10 mmol) in 20 ml of methylene chloride at −10° C. A solution of 2 g (10 mmol) of 4-hydroxybenzophenone in 10 ml of methylene chloride was added. The mixture was stirred for 0.5 h at −10°~0° C. for 2 h. The reaction mixture was allowed to stand at 25° C. overnight, then filtered by suction. The filtrate was stripped of the solvent, taken up with 1:1 ethyl acetate-ether, and filtered again. The final filtrate was concentrated and the residue was recrystallized from ethyl acetate to give 2.2 g (68%) of the title compound; M.P.~137°-138° C.

Calcd. for $C_{19}H_{19}NO_4$: C, 70.14; H, 5.89; N, 4.30. Found: C, 69.96; H, 6.03; N, 4.53.

EXAMPLE 19

4-(2-methyl-2-carboxy-propionyloxy)-benzophenone

To a solution of 2 g (12 mmol) of dimethylmalonyl chloride in 19 ml of methylene chloride, a solution of 2 g (10 mmol) of 4-hydroxybenzophenone in 10 ml of pyridine was added over 15 min at −5° C. The mixture was stirred at 0° C. for 0.5 h, allowed to warm to 25° C. over 1 h, then stripped of the solvent, and finally stirred with 1:1 ethyl acetate-water for 1.5 h at 25° C. The organic phase was washed with cold 2% hydrochloric acid, then with water, and finally extracted with 5% sodium bicarbonate solution. The aqueous extract was acidified to pH 3 and filtered to collect crude product, which was purified by recrystallization from EtOH-water to yield the title compound. 0.325 g (10%); M.P.~147°-150° C.

Calcd. for $C_{18}H_{16}O_5$: C, 66.49; H, 5.12. Found: C, 66.38; H, 4.94.

EXAMPLE 20

4-(2-methyl-2-carbomethoxy-propionyloxy)-benzophenone

This compound was obtained by treating the compound of the previous Example with diazomethane followed by a recrystallization from ethanol. Yield, 40%; M.P.~121°-122° C.

Calcd. for $C_{19}H_{18}O_5$:C, 69.92; H, 5.56. Found: C, 69.97; H, 5.52.

EXAMPLE 21

4,4'-dipivaloyloxy-benzhydrol

An ethanolic solution (60 ml) of 1.0 g of 4,4'-dipivaloylbenzophenone was treated with 67 mg of sodium borohydride initially at 0° C., later at 25° C. overnight. The reaction mixture was cooled to 0° C., treated with acetic acid to remove excess borohydride, stripped of the solvent, and taken up with ether. A chromatographic separation on a silica gel column using toluene-ethyl acetate gave 0.47 g (47%) of product; M.P.~148.5°-152.5° C.

Calcd. for $C_{23}H_{28}O_5$: C, 7.185; H, 7.34. Found: C, 7.177; H, 7.52.

EXAMPLE 22

Sodium 3-[(4,4'-dipivaloyloxy-benzhydryl)-oxycarbonyl]propionate

A solution of 500 mg of the compound from the previous example, 260 mg of succinic anhydride, and 160 mg of 4-(dimethylamino)-pyridine in 2 ml of pyridine was allowed to stand for 2 days. The reaction mixture was stripped of the solvent, taken up with ethyl acetate, washed with sodium bicarbonate solution, washed with brine, and dried on $Na_2SO_4$. Evaporation of the solvent left 319 mg (51%) of the product salt which did not melt up to 270° C.

Calcd. for $C_{27}H_{31}O_8Na$: C, 64.02; H, 6.17; Na, 4.54. Found: C, 63.78; H, 6.08; Na, 4.67.

EXAMPLE 23

4-methallyloxybenzophenone

A mixture of 34 g of 4-hydroxybenzophenone, 1.0 g of sodium iodide, 18.7 ml of methallyl chloride, and 25 g of potassium carbonate in 350 ml of acetone was refluxed for 96 h. After cooling the reaction mixture was filtered, concentrated, dissolved in methylene chloride, washed with sodium hydroxide solution, washed with water, dried over magnesium sulfate, and concentrated to obtain crystalline product; 41.6 g; M.P.~85°-86.5° C.

Calcd for $C_{17}H_{16}O_2$: C, 80.93; H, 6.39. Found: C, 81.15; H, 6.40.

EXAMPLE 24

3-methyallyl-4-hydroxybenzophenone

A mixture of 38.0 g of the compound from the previous Example and an equal amount of diethylaniline was heated to 207°-218° C. for 3.5 h. The reaction mixture was taken up with methylene chloride, washed with 2M sulfuric acid, washed successively with water, with 5% potassium hydroxide, with water, and then dried (MgSO$_4$) and concentrated to give 27.8 g of title compound; M.P.~131°–133° C.

EXAMPLE 25

3-methallyl-4-pivaloyloxybenzophenone

This substance (36 g) was prepared from the compound of the previous Example (29 g) using the procedure of Example 1. Oil.

Calcd. for $C_{22}H_{24}O$: C, 78.54; H, 7.19. Found: C, 78.48; H, 7.31.

EXAMPLE 26

3-allyl-4-pivaloyloxybenzophenone 4-hydroxybenzophenone (25 g) was converted to 4-allyloxybenzophenone (29.2 g, yellow solid) by the procedure of Example 23. Claisen rearrangement using that procedure gave 13.5 g (47%) of desired 3allyl-4-hydroxybenzophenone, the balance being recovered. Finally, acylation of 3-allyl-4-hydroxybenzophenone (5.9 G) according to general procedure of Example 1 produced 6.9 g (86%) of product as yellow solid.

Calcd. for $C_{21}H_{22}O_3$: C, 78.23; H, 6.88. Found: C, 78.88; H, 6.92.

EXAMPLE 27

3-(1-methyl-allyl)-4-pivaloyloxybenzophenone 4-crotyloxybenzophenone was prepared from 4-hydroxybenzophenone and crotyl bromide using the procedure of Example 23. Through Claisen rearrangement it was converted into 3-($\alpha$-methyl-allyl)-4-hydroxybenzophenone. The crude product (10.1 g) was acylated (procedure of Example 1) and purified by chromatography (40:60 hexane-methylene chloride on silica gel) to produce 12.25 g (91%) of oil.

Calcd. for $C_{22}H_{24}O_3$: C, 78.54; H, 7.19. Found: C, 78.40; H, 7.16.

EXAMPLE 28

3-(2-methyl-3-hydroxypropyl)-4-pivaloyloxybenzophenone

A solution of 15.0 g of 3-methallyl-4-pivaloyloxybenzophenone in 30 ml of THF was treated with 100 ml of 0.5M solution of 9-BBN in THF at 0° C. The mixture was stirred at 25° C. for 3 h and at 50° C. for 1 h. To the cooled reaction mixture were added 30 ml of ethanol, 9.5 ml of 6N sodium hydroxide, and 18 ml of 30% hydrogen peroxide. After stirring at 25° C. for 2 h, the oxidation mixture was treated with solid potassium carbonate followed by a small amount of water. The organic layer was separated and dried over MgSO$_4$. The crude product (22 g) was chromatographed on a silica gel column using toluene-ethyl acetate. 8.0 g of product was obtained as an oil. Calcd. for $C_{22}H_{26}O_4$: C, 74.55; H, 7.39. Found: C, 74.30; H, 7.35.

EXAMPLE 29

3-(3-hydroxyoropyl)-4-pivaloyloxybenzophenone

Using the procedure of Example 28, 2.0 g of the compound of Example 26 was hydroborated to yield 1.48 g of oily product (after chromatography.)

Calcd. for $C_{21}H_{24}O_4$: C, 74.09; H, 7.11. Found: C, 74.51; H, 7.15.

EXAMPLE 30

3-(2-formyl-propyl)-4-pivaloyloxy-benzophenone

To a solution of 1.8 ml of oxalyl chloride in 43 ml of methylene chloride were added dropwise a solution of 3.0 ml of DMSO in 9 ml of methylene chloride at −60° C., and then a solution of 6.14 g of 3-(2-methylhydroxy-propyl-4-pivaloyloxybenzophenone in 17 ml of methylene chloride. The mixture was stirred at about 31 50°–60° C. for 15 min, then treated with 12.1 ml of triethylamine. The reaction mixture was stirred at −50° C. for 5 min, warmed to 25° C., and then treated with 85 ml of water. The organic layer was washed with dilute hydrochloric acid and then with brine, dried (MgSO$_4$) and concentrated to give 5.0 g of product as an oil.

Calcd. for $C_{22}H_{24}O_4$: C, 74.97; H, 6.86. Found: C, 74.66; H, 6.95.

EXAMPLE 31

3-(2-carboxy-propyl)-4-pivaloyloxybenzophenone

To a stirred mixture of 0.50 g of the compound from the previous example and 0.212 g of NH$_2$SO$_3$H in 55 ml of water 0.172 g of sodium chlorite was added. After 0.5 h the reaction mixture was extracted with ether. The ethereal extract (dried over Na$_2$SO$_4$) gave 0.52 g of title compound; M.P.~119°–120° C.

Calcd. for $C_{22}H_{24}O_5$: C, 71.72; H, 6.57. Found: C, 71.83; H, 6.53.

EXAMPLE 32

3-(2-carboxyethyl)-4-pivaloyloxybenzophenone

A solution of 1.01 g of 3-(hydroxypropyl)-4-pivaloyloxybenzophenone in 40 ml of acetone was treated with 1.5 ml of 8N Jones' Reagent at 0° C. for 1 h. The reaction mixture was treated with 5 ml of isopropyl alcohol and filtered to remove inorganic material. The filtrate was evaporated and the residue was taken up with toluene. The toluene phase was extracted with 3% KHCO$_3$ solution and the aqeuous extract was acidified to pH 2. The acidic product was extracted with ethyl acetate. The ethyl acetate extact was washed with brine, dried (MgSO$_4$), and concentrated to give 0.784 mg (74%) of product.

Calcd. for $C_{21}H_{22}O_5$: C, 71.17; H, 6.24. Found: C, 70.95; H, 6.28.

EXAMPLE 33

3-($\alpha$-carboxy-ethyl)-4-pivaloyloxybenzophenone

A solution of 5.05 g of 3(1-methylallyl)-4-pivaloyloxybenzophenone in 40 ml ethanol was treated with 7.23 g of sodium periodate in 30 ml of water and 0.5 mg of osmium tetroxide at 25° C. for 4 h. The reaction mixture was filtered and the filtrate was concentrated. The residue was taken up with ether, washed with brine, dried (MgSO$_4$) and concentrated to give 5.1 g of crude aldehyde. A flash chromatography produced 2.98 g (59%) of pure aldehyde which was dissolved in 20 ml of acetone and oxidized with 2.0 ml of 8N Jones' reagent at 0° C. Extractive work-up afforded 1.57 g (50%); M.P.~109°–112.5° C.

Calcd. for $C_{21}H_{22}O_5$: C, 71.13; H, 6.26. Found: C, 70.93; H, 6.27.

EXAMPLE 34

4-isobutyryloxybenzophenone

To a solution of 8.5 g of 4-hydroxybenzophenone in 75 ml of dry pyridine 6.75 ml of isobutyric chloride was added at 0°~10° C. The reaction mixture was allowed to stand at 25° C. for 2 h, poured into ice water. The precipitate was collected by suction and recrystallized from ethanol; M.P.~69°-69.5° C.

Analysis Calcd. for $C_{17}H_{16}O_3$: C, 76.10; H, 6.01. Found: C, 75.72; H, 6.00.

EXAMPLE 35

4-propionyloxybenzophenone

The title compound was prepared using propionyl chloride in place of isobutyryl chloride in the procedure of the previous example; M.P.~53.5°-54.5° C.

Analysis Calcd. for $C_{16}H_{14}O_3$: C, 75.58; H, 5.55. Found: C, 75.12; H, 5.52.

EXAMPLE 36

4-cyclohexanoyloxybenzophenone

The title compound was prepared from 6.0 g of 4-hydroxybenzophenone, 6.0 ml of cyclohexanecarbonyl chloride, pyridine (70 ml). Recrystallized from ethyl acetate-ethanol-water; M.P.~111°-112° C.

Analysis Calcd. for $C_{20}H_{20}O_3$: C, 77.90; H, 6.54. Found: C, 77.62; H, 6.46.

EXAMPLE 37

4-cyclopropanecarbonyloxybenzophenone

Prepared from 6.0 g of 4-hydroxybenzophenone and 4.1 ml of cyclopropanecarbonyl chloride in 70 ml of pyridine. Recrystallized from ethyl acetate-ethanol-water mixture; M.P.~81°-81.5° C.

Analysis Calcd. for $C_{17}H_{14}O_3$: C, 76.68; H, 5.30. Found: C, 76.36; H, 5.28.

EXAMPLE 38

4-methacryloyloxybenzophenone

Prepared from 6.0 g of 4-hydroxybenzophenone and 4.4 ml of methacryloyl chloride in 70 ml of pyridine. Recrystallized from ethyl acetate-ethanol-water; M.P.~69.5°-70.5° C.

Analysis Calcd. for $C_{17}H_{14}O_3$: C, 76.68; H, 5.30. Found: C, 76.73; H, 5.35.

EXAMPLE 39

4,4'-dipivaloyloxydiphenylmethane

A solution of 1.0 g (0.005 mole) of 4,4'-dihydroxydiphenylmethane and 1.4 g (0.015 mole) of pivaloyl chloride was warmed to 50° C. in 20 mls of pyridine with a drying tube attached. 100 mls of water was added and the crystals filtered and recrystallized from ethanol. 1.4 g (75%) of the title compound was obtained; M.P.~130°-133° C.

Analysis Calcd. for $C_{23}H_{28}O_4$: C, 74.97; H, 7.66. Found: C, 74.86; H, 7.69.

EXAMPLE 40

4,4'-diisobutyryloxybenzophenone

To a solution of 5.0 g of dihydroxybenzophenone in 60 ml of pyridine 6.0 ml (2.4 equivalent) of isobutyryl chloride was added and the reaction mixture maintained at 25° C. The reaction mixture was then poured into ice water. The colorless precipitates were filtered by suction and recrystallized from ethanol; M.P.~143.5°-144.5° C.

Anal. calcd. for $C_{21}H_{22}O_5$: C, 71.17; H, 6.27. Found: C, 71.07; H, 6.24.

EXAMPLE 41 (PRIOR ART)

4-acetyloxybenzophenone

The title compound was prepared from 4-hydroxybenzophenone and acetyl chloride in pyridine and recrystallized from ethanol (M.P.~82°-83.5° C.). See J. Chem. Soc., 2867 (1927).

The preferred compounds of the invention were evaluated for biological activity, i.e., elastase inhibitory/anti-inflammatory activity, by determining the elastase inhibitory effects of the compounds pursuant to the following test procedure.

EXAMPLE 42

Inhibition of Human Leukocyte Elastase (HLE)

This test measures the rate of hydrolysis of Methoxysuccinyl-Alanyl-Alanyl-Prolyl-Valyl-nitroanilide by HLE in the presence and absence of the compound to be tested. The procedure used is as follows. The following stock solutions are prepared:

1. a saline solution of HLE prepared from a composition containing 10% HLE with the remainder being sodium acetate (300 micrograms per ml) wherein the concentration was adjusted to give a change in absorption of 0.12 od units per minute in the assay in the absence derivative,
2. a dimethylsulfoxide solution of the nitroanilide peptide (2 m mole),
3. tris-HCl buffer (0.2M,pH 8.0) and
4. a dimethylsulfoxide solution of the derivative to be tested at 20 times the desired final concentration as indicated by the concentration codes given after Table 3 infra.

The test hydrolysis solution was then prepared by adding 850 microliters buffer, 50 microliters derivative solution, 50 microliters peptide solution and 50 microliters of HLE solution to a 1 cm. semi-micro cuvette. The cuvette was capped, slightly shaken and placed in the light chamber of a recording colorimeter where the increase in absorption at 410 nm. due to liberated nitroaniline was measured. Using this procedure, the one minute change in absorption of the test sample containing derivative was compared to the change in absorption in the absence of derivative. A 20% or more decrease in the rate of absorption was interpreted as a positive inhibition.

The results with respect to certain of the preferred compounds of the invention are given in Table I below. The results indicate that the compounds of formulas I and II are generally active at the concentrations indicated (active compound concentration to obtain at least 50% elastase inhibition).

TABLE I

| Compound Example No. | Inhibition of Elastase $IC_{50}$, [Molar] |
| --- | --- |
| 1 | $6.2 \times 10^{-7}$ |
| 1a | $6.0 \times 10^{-8}$ |
| 2 | $5.5 \times 10^{-8}$ |
| 3 | $2.7 \times 10^{-8}$ |
| 4 | $1.3 \times 10^{-7}$ |
| 6 | $2.9 \times 10^{-7}$ |
| 7 | $6.7 \times 10^{-7}$ |
| 9 | $3.6 \times 10^{-7}$ |

TABLE I-continued

| Compound Example No. | Inhibition of Elastase IC$_{50}$, [Molar] |
| --- | --- |
| 13 | $8.4 \times 10^{-8}$ |
| 14 | $9.0 \times 10^{-7}$ |
| 16 | $4.6 \times 10^{-7}$ |
| 17a | $8.3 \times 10^{-8}$ |
| 25 | $8.5 \times 10^{-8}$ |
| 26 | $8.0 \times 10^{-7}$ |
| 27 | $3.2 \times 10^{-7}$ |
| 29 | $3.5 \times 10^{-7}$ |
| 34 | $2.5 \times 10^{-7}$ |
| 39 | $4.5 \times 10^{-7}$ |
| 40 | $1.5 \times 10^{-7}$ |

While the invention has been described and illustrated with reference to certain preferred embodiments thereof, those skilled in the art will appreciate that various changes, modifications and substitutions can be made therein without departing from the spirit of the invention. For example, effective dosages other than the preferred ranges set forth hereinabove may be applicable as a consequence of variations in the responsiveness of the patient being treated, severity of the inflammatory condition, i.e., emphysema, rheumatoid arthritis and similar elastase mediated conditions, dosage dependent adverse effects, if any, observed and analogous considerations. Likewise, the specific pharmacological response observed may vary depending upon the particular active compounds selected or whether different active compounds are used in combination or in the presence of suitable pharmaceutical carriers, as well as the type of formulation and mode of administration employed, and such expected variations or differences in results are specifically contemplated in accordance with the objects and practices of the present invention. It is intended, therefore, that the invention be limited only by the scope of the claims which follow.

What is claimed is:

1. A pharmaceutical composition for the treatment of elastase mediated diseases comprising a pharmaceutically acceptable inert carrier in combination with an elastase inhibitory anti-inflammatory effective amount of a compound selected from 4-pivaloyloxybenzophenone; 4,4'-dipivaloyloxybenzophenone; 4,4'-diisobutyryloxybenzophenone; 2,4,4'-tripivaloyloxybenzophenone; 2,2',4,'-tetrapivaloyloxy benzophenone; 4,4'-dipivaloyloxyazobenzene; 4-pivaloyloxy-4'-chlorobenzophenone; 4,4'-α,α-dimethylvaleroyloxybenzophenone; 3,4,5,4',5',6'-hexapivaloyloxybenzophenone; 2,4-dipavaloyloxybenzophenone; 4,4'-di(t-butyl)oxycarbonyloxybenzophenone; 4,4'-dipivaloyloxydiphenylether; 4,4'-dipivaloyloxydiphenylsulfone; 3-methylallyl-4-pivaloyloxybenzophenone; 3-allyl-4-pivaloyloxybenzophenone; 3-(1-methylallyl)-4-pivaloyloxybenzophenone; 3-(3-hydroxypropyl)-4-pivaloyloxybenzophenone; 4-isobutyryloxybenzophenone; 4,4'-dipivaloyloxydiphenylmethane.

* * * * *

UNITED STATES PATENT AND TRADEMARK OFFICE
CERTIFICATE OF CORRECTION

PATENT NO. : 4,801,610
DATED : Jan. 31, 1989
INVENTOR(S) : Miyano et al.

It is certified that error appears in the above-identified patent and that said Letters Patent is hereby corrected as shown below:

Column 2, line 56, reading "$C_2$-$C_4$ alkyl, $C_1$-$C_4$ alkenyl" should read -- $C_1$-$C_4$ alkyl, $C_2$-$C_4$ alkenyl --.

Column 4, line 67, reading "$C_2$-$C_4$ alkenyl" should be deleted.

Column 9, line 54, reading "(1973)" should read -- (1972) --.

Column 10, lines 7-8, reading "U.S. Pat. No. 4,195,025" should read -- U.S. Pat. No. 4,195,023 --.

Column 10, line 39, reading "inhiit" should read -- inhibit --.

Column 17, line 21, reading "3allyl-4-" should read -- 3-allyl-4- --.

Column 17, line 48, reading "9-BBN" should read -- 9-borabicyclo-[3.3.1]nonane --.

Column 17, line 62, reading "3-(3-hydroxyoropyl)-" should read -- 3-(3-hydroxypropyl)- --.

Column 18, lines 10-11, reading "31 50°-60°C." should read -- -50-60°C --.

Column 22, line 17, reading "2,2',4,'-" should read -- 2,2',4,4'- --.

Signed and Sealed this

Twelfth Day of March, 1991

Attest:

HARRY F. MANBECK, JR.

Attesting Officer

Commissioner of Patents and Trademarks